United States Patent [19]

Schwartz et al.

[11] 4,046,763

[45] Sept. 6, 1977

[54] 2,3-DIPHENYL-5-ETHYLPYRAZINE

[75] Inventors: Norman Schwartz, Philadelphia; Richard J. Mohrbacher, Fort Washington, both of Pa.

[73] Assignee: McNeil Laboratories, Incorporated, Fort Washington, Pa.

[21] Appl. No.: 307,684

[22] Filed: Nov. 17, 1972

Related U.S. Application Data

[62] Division of Ser. No. 774,486, Nov. 8, 1968, Pat. No. 3,761,477.

[51] Int. Cl.$^2$ .......................................... C07D 241/12
[52] U.S. Cl. ................................. 260/250 B; 424/250
[58] Field of Search ................................. 260/250 B

[56] References Cited

U.S. PATENT DOCUMENTS

| 3,006,918 | 10/1961 | de Jongh et al. | 260/250 R |
| 3,901,885 | 8/1975 | Schwartz et al. | 260/250 B |
| 3,901,886 | 8/1975 | Schwartz et al. | 260/250 B |
| 3,928,347 | 12/1975 | Schwartz et al. | 260/250 B |

*Primary Examiner*—Nicholas S. Rizzo
*Attorney, Agent, or Firm*—Salvatore R. Conte; Geoffrey G. Dellenbaugh

[57] ABSTRACT

The compound 2,3-diphenyl-5-ethyl-pyrazine, useful as a precursor in the synthesis of those compounds of the class of pyrazine, arylpyrazine, diphenylpyrazine, and cycloalkylpyrazine malonates, acetates, acetamides, and acetic acids, useful for their ultraviolet light absorption properties.

1 Claim, No Drawings

2,3-DIPHENYL-5-ETHYLPYRAZINE

This is a divisional application of my co-pending application Ser. No. 774,486, filed Nov. 8, 1968 and now U.S. Pat. No. 3,761,477.

This invention relates to certain novel pyrazineacetic acids, acetates, and acetamides. More particularly, this invention is concerned with arylpyrazine and cycloalkylpyrazine malonates, acetates, acetamides, and acetic acids having the formulae

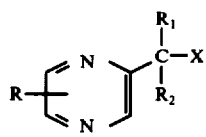

(I)

wherein R is a member selected from the group consisting of phenyl, chlorophenyl, dichlorophenyl, fluorophenyl, trifluoromethylphenyl, loweralkoxyphenyl, diloweralkoxyphenyl, loweralkylphenyl, diloweralkylphenyl, cyclohexyl and cyclopentyl; $R_1$ is a member selected from the group consisting of hydrogen and loweralkyl; $R_2$ is a member of the group consisting of hydrogen, loweralkyl, loweralkyl carboxylate ester, and sodium, calcium, and ammonium carboxylate salts; and X is a member selected from the group consisting of loweralkyl carboxylate ester, carboxylic acid, carboxamide, a member selected from the group consisting of N-loweralkyl-, N,N-diloweralkyl, N-aryl-, N-aralkyl-, and N-heterocyclic-substituted carboxamides, and sodium, calcium and ammonium carboxylate salts; wherein when $R_2$ is respectively loweralkyl carboxylate ester or carboxylate salt, X is also respectively loweralkyl carboxylate ester or carboxylate salt.

This invention is also concerned with pyrazine malonates, acetates, and acetic acids having the formula:

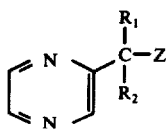

(II)

wherein $R_1$ is a member selected from the group consisting of hydrogen and loweralkyl; $R_2$ is a member selected from the group consisting of hydrogen, loweralkyl, loweralkyl carboxylate ester, and sodium, calcium, and ammonium carboxylate salts; and Z is a member selected from the group consisting of loweralkyl carboxylate ester, carboxylic acid, and sodium, calcium, and ammonium carboxylate salts; wherein when $R_2$ is respectively loweralkyl carboxylate ester or carboxylate salt, Z is also respectively loweralkyl carboxylate ester or carboxylate salt.

This invention is further concerned with diphenylpyrazine malonates, acetates, acetamides and acetic acids having the formula:

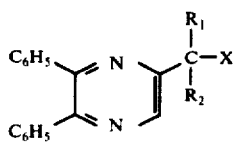

(III)

wherein $R_1$ is a member selected from the group consisting of hydrogen and loweralkyl; $R_2$ is a member selected from the group consisting of hydrogen, loweralkyl, loweralkyl carboxylate ester, and sodium, calcium, and ammonium carboxylate salts; X is a member selected from the group consisting of loweralkyl carboxylate ester, carboxylic acid, carboxamide, a member selected from the group consisting of N-loweralkyl-, N,N-diloweralkyl, N-aryl-, N-aralkyl-, and N-heterocyclic-substituted carboxamides, and sodium, calcium, and ammonium carboxylate salts; and wherein when $R_2$ is respectively loweralkyl carboxylate ester or carboxylate salt, X is also respectively loweralkyl carboxylate ester or carboxylate salt.

The term "loweralkyl" includes alkyl groups containing 1 to 7 carbon atoms, and preferably 1 to b 4 carbon atoms, including saturated aliphatic chains, straight or branched, such as methyl, ethyl, propyl, isopropyl, n-butyl, and isobutyl.

The compounds of this invention absorb ultraviolet light and are useful as sun-screening materials in salves and ointments. In addition, because of their solubility in organic materials generally, they may be used as ultraviolet absorbers in plastics and resins, such as polystyrene, polyethylene, polypropylene, polyacrylics (methacrylate resins, polyacylamides, polyacrylonitrile fibers), polyamide fibers (nylon e.g.), and polyester fibers. In the latter use, the inclusion of 0.01 to 5 percent of the absorber, based on the polymer weight, is sufficient to render protection against ultraviolet light, such as in plastic film or light filters. The absorber may be incorporated in the mixtures of monomers before polymerization to form the polymer or it may be incorporated in the polymer at any stage during its handling, as by milling into the polymer together with other compounding ingredients or during the spinning of polymers into fibers, etc.

Due to the asymmetric center present in the subject compounds wherein $R_1$ and $R_2$ are different, except where $R_2$ is identical with X or Z, it is evident that the existence of such compounds in the form of resolved enantiomorphs is possible. It is naturally intended that such enantiomorphs are included within the scope of this invention.

Compounds of Formula I and Formula II, wherein $R_1$ is hydrogen or loweralkyl, $R_2$ is loweralkyl carboxylate, and X or Z is loweralkyl carboxylate are prepared by reacting the appropriate 2-chloropyrazine derivative with diloweralkyl malonate or diloweralkyl loweralkylmalonate in the presence of sodium hydride in a suitable solvent such as dimethylformamide. As an alternative process, sodamide and liquid ammonia may be employed in place of sodium hydride and dimethylformamide.

Compounds of Formula I and Formula II wherein $R_1$ and $R_2$ are both hydrogen or $R_1$ is hydrogen and $R_2$ is loweralkyl and X or Z is loweralkyl carboxylate are prepared by heating the foregoing diloweralkyl pyrazinylmalonate and diloweralkyl α-loweralkylpyrazinylmalonate derivatives in a suitable solvent such as dimethyl sulfoxide in the presence of sodium cyanide.

Compounds of Formula I and Formula II wherein $R_1$ and $R_2$ are both hydrogen or $R_1$ is hydrogen and $R_2$ is loweralkyl and X or Z is carboxylic acid are prepared by refluxing the foregoing loweralkyl pyrazineacetate and loweralkyl α-loweralkylpyrazineacetate derivatives in aqueous sodium hydroxide and acidifying the resulting hydrolyzate. In an alternative procedure, the pyrazineacetic acid derivatives may be prepared by treating the diloweralkyl pyrazinylmalonates and the diloweralkyl α-loweralkylpyrazinylmalonates of Formula I and Formula II with a base such as aqueous sodium hydroxide, and thereafter acidifying the solution.

Compounds of Formula I wherein X is carboxamide are prepared by reacting the aforesaid pyrazineacetate and α-loweralkylpyrazineacetate derivatives with ammonium hydroxide.

In an alternative procedure, loweralkyl esters of the acetic acids of Formula I and Formula II may be prepared from the corresponding acids by conventional esterification procedures. In another alternative procedure, the acetamides of Formula I may be reacted with aqueous hydrochloric acid, avoiding excess temperatures, or with sodium or ammonium hydroxide and thereafter, acidifying to form the corresponding pyrazineacetic acid derivatives.

Compounds of Formula I and II wherein $R_1$ and $R_2$ are each loweralkyl and X or Z are loweralkyl carboxylate are prepared by reacting a loweralkyl halide, such as methyl, ethyl, isopropyl or n-butyl iodide, with the aforementioned loweralkyl α-loweralkylpyrazineacetates in the presence of sodamide in liquid ammonia. As an alternative, the loweralkyl α-loweralkylpyrazineacetates may be reacted with sodium hydride in dimethylsulfoxide followed by reaction of the anion thus produced with a loweralkyl halide, preferably the iodide.

The compounds of Formula I and II wherein $R_1$ and $R_2$ are each loweralkyl and X or Z are loweralkyl carboxylate may be converted to the corresponding acetamides and acetic acids by the procedures described hereinbefore for the compounds wherein $R_1$ is loweralkyl and $R_2$ is hydrogen.

The N-substituted acetamides of this invention may be prepared by reacting the corresponding acetic acid derivatives of this invention with thionyl chloride and then with the desired amine.

The salts of the acetic acid derivatives of this invention may be prepared by reacting the corresponding acid in water with sodium, calcium, or ammonium hydroxide.

Compounds of the Formula III are prepared in the same manner as in the case of compounds of Formula I and Formula II, using 5-chloro-2,3-diphenylpyrazine as the starting material.

The following schematic diagram, exemplifying the preparation of Formula I type compounds, illustrates the foregoing syntheses:

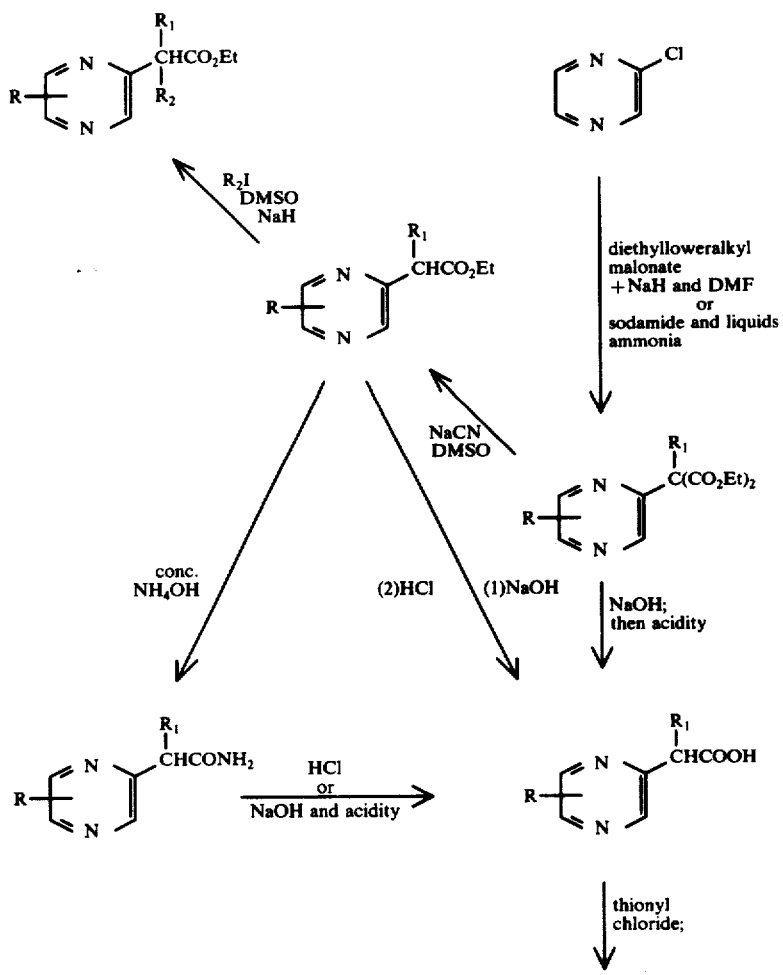

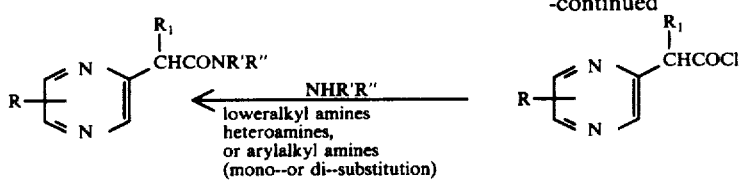
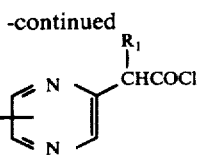

The following schematic diagram illustrates the preparation of the starting materials used in the synthesis of the novel compounds of this invention:

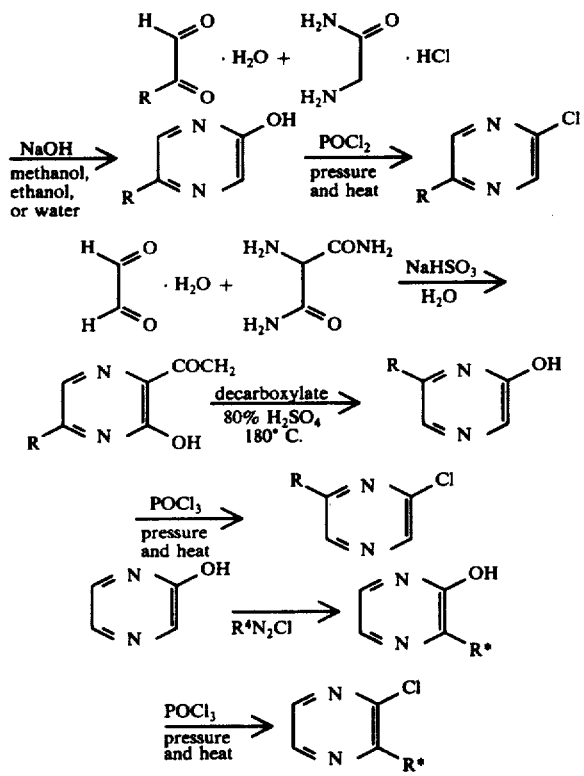

*Except when R is cycloalkyl.

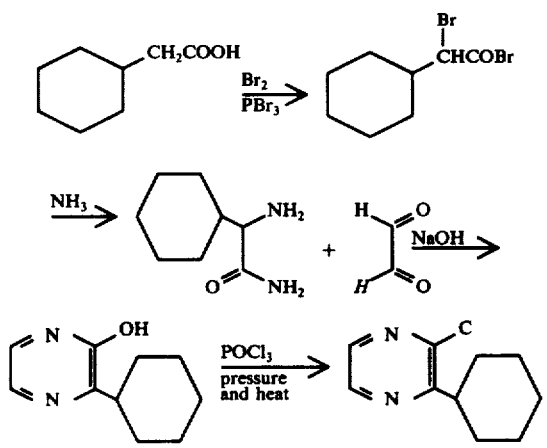

The following examples are intended to illustrate, but not to limit, the scope of the present invention.

EXAMPLE I

To a mixture of phenylglyoxal hydrate (41.5 g., 0.27 mole) in 250 ml. of methanol at −40° (dry ice-carbon tetrachloride-acetone) is added, with stirring, glycinamide hydrochloride (30.0 g., 0.27 mole) in 250 ml. of methanol, precooled to −40° C. To this stirred mixture 50 ml. of 12.5 N sodium hydroxide is added dropwise while the temperature is maintained at −30° C. The temperature is raised to between −20° and −10° for ½ hour, to 0° for 2 hours, and finally to room temperature for 2 hours. The reaction mixture is then cooled in an ice-bath and treated dropwise with 45 ml. of concentrated hydrochloric acid. The pH of the mixture is adjusted to 5 by the portionwise addition of 27 g. of sodium bicarbonate. The mixture is filtered. The solid material is recrystallized from n-butanol. The product is 5-phenylpyrazinol; m.p. 208°–210° C.

EXAMPLE II p-Chlorophenylglyoxal hydrate is prepared in two steps from α-bromo-p-chloroacetophenone as described by Kornblum and Frazier [J. Am. Chem. Soc., 88, 865 (1966)]. To the p-chlorophenylglyoxal hydrate (26.5 g., 0.14 mole) in 130 ml. of methanol cooled to −30° is added, with stirring, glycinamide hydrochloride (15.7 g., 0.14 mole) in 130 ml. of methanol precooled to −30° C. To the stirring mixture is added dropwise 26 ml. of 12.5 N sodium hydroxide while the temperature is raised and is maintained at −5° to 0° C. for 2 hours. The mixture is then stirred at ambient temperature for 2½ hours. Concentrated hydrochloric acid (24 ml.) is added dropwise to the mixture with ice-bath cooling. This is followed by the portionwise addition of sodium bicarbonate (15 g.). The reaction mixture is refrigerated overnight, filtered and the solid is washed with water and recrystallized from 95 percent ethanol. The product is 5-(p-chlorophenyl)pyrazinol; m.p. 218–221° C.

EXAMPLE III

To phosphorous oxychloride (70 ml.) containing sulfuric acid (4 drops) in a pressure bottle is added 5-phenylpyrazinol (18.3 g., 0.106 mole), with swirling. The open bottle is heated at 125° C. for ½ hour to allow the evolution of hydrogen chloride. The bottle is closed and the mixture is heated at 125° C. for 5 hours. The bottle is cooled and the reaction solution is poured onto a stirred mixture of 700 g. of ice and 300 ml. of chloroform. After about 20 minutes, the mixture is cooled in an ice-salt bath and slowly neutralized with concentrated ammonium hydroxide, followed by the addition of 50% sodium hydroxide to make the mixture basic. The mixture is filtered through celite, the layers are separated, and the aqueous layer is extracted twice more with chloroform. The combined chloroform extracts are dried ($Na_2SO_4$) and evaporated. The solid material is recrystallized from methanol. The product obtained is 2-chloro-5-phenylpyrazine; m.p. 96°–98° C.

EXAMPLE IV

A sodium hydride-mineral oil suspension (54%, 28 g., 0.62 mole) is stirred with three 150 ml. portions of dry hexane ($Na_2SO_4$), each portion being pipetted out to remove the mineral oil. Dimethylformamide (previously distilled and dried over a molecular sieve; 180 ml.) is added through a pressure equalized addition funnel while a slow stream of nitrogen is passed through the mixture. The reaction vessel is cooled in an ice-bath and diethylmethylmalonate (99.5 g., 0.57 mole) is added dropwise to the stirred mixture. After addition is complete, the ice-bath is replaced by an oil bath and the temperature is raised to 50° C. A solution of chloropyrazine (50 g., 0.44 mole) in dimethylformamide (50 ml.) is added dropwise. The mixture is then heated for 3 hours, raising the temperature during this period to 120° C.

The reaction mixture is cooled to about 70° C. and water (20 ml.) is added. The mixture is concentrated to a small volume and the residual liquid is diluted with ice-water (300 ml.) and extracted several times with ether. The combined ether extracts are washed with 5% hydrochloric acid, then with water, dried, and evaporated. The resulting liquid is distilled. The product obtained is diethyl α-methylpyrazinylmalonate; b.p. 114°–118° C. (0.5 mm.).

EXAMPLE V

A sodium hydride-mineral oil suspension (54%; 3.1 g., 0.069 mole) is stirred with three 50 ml. portions of dry hexane, each portion being pipetted out to remove the mineral oil. Dimethylformamide (30 ml., previously distilled and dried over a molecular sieve) is added through a pressure equalized addition funnel while a slow stream of nitrogen is passed through the mixture. The reaction vessel is cooled in an ice-bath while diethyl methylmalonate (12 g., 0.069 mole) is added dropwise to the stirred mixture. After the addition is complete, the ice-bath is replaced by an oil bath and the temperature is raised to 50° C. To the mixture is added dropwise 2-chloro-5-phenylpyrazine (10 g., 0.053 mole) in warm dimethylformamide (55 ml.). After this addition is complete, the mixture is heated for 3½ hours during which time the temperature is raised to 120° C. The reaction mixture is cooled to about 80° C. and water (4 ml.) is added. The mixture is concentrated to a small volume, and the residual liquid is diluted with 50 g. of ice and extracted with ether several times. The combined ether extracts are washed with 5% hydrochloric acid, then with water, and then dried and evaporated. The resulting oil is chromatographed on a column of 500 g. of Merck acid-washed alumina. Elution with benzene-hexane (4:1) through ethyl acetate-benzene (1:3) yielded diethyl α-methyl-5-phenylpyrazinylmalonate.

EXAMPLE VI

A mixture of diethyl α-methyl-5-phenylpyrazinylmalonate (10.3 g., 0.031 mole) and sodium cyanide (3.2 g., 0.065 mole) in dimethyl sulfoxide (120 ml.) is stirred and heated at 130° C. for ¾ hour. The reaction mixture is poured onto 300 g. of ice saturated with sodium chloride, and extracted several times with ether. The combined ether extracts are washed with water, dried, and evaporated. The resulting material is triturated with warm hexane and filtered. The hexane filtrate is evaporated and the resulting oil is distilled. The third fraction, which solidifies, is recrystallized from pentane and filtered at dry ice temperature. The product obtained is ethyl α-methyl-5-phenylpyrazineacetate; m.p. 38°–40° C.

EXAMPLE VII

A mixture of diethyl α-methylpyrazinylmalonate, (20 g., 0.08 mole) and sodium cyanide (8 g., 0.16 mole) in dimethyl sulfoxide (150 ml.) is stirred and heated between 125°–160° C. for 1 hour. The reaction mixture is poured into 400 ml. of ice water saturated with sodium chloride, and the mixture is extracted several times with ether. The ether extracts are combined and washed with water until neutral, dried, and evaporated. The resulting liquid is distilled. The product obtained is ethyl α-methylpyrazineacetate; b.p. 71°–73° C. (0.4 mm.).

EXAMPLE VIII

A mixture of diethyl α-methylpyrazinylmalonate (20 g., 0.08 mole), in 50% sodium hydroxide (40 ml.) is stirred and refluxed for 1¼ hours. The solution is cooled to room temperature, washed with ether, acidified, saturated with sodium chloride, and extracted several times with ether. The combined ether extracts are dried and evaporated. The solid material is recrystallized by dissolving in warm benzene (with temperature below 50° C.) and then concentrating the solution under a stream of nitrogen with temperature below 50° C. The resulting mixture is filtered. The product obtained is α-methylpyrazineacetic acid; m.p. 95–96° C. dec.

EXAMPLE IX

A mixture of ethyl α-methyl-5-phenylpyrazineacetate (1.0 g., 0.0039 mole), water (8 ml.), and 50% aqueous sodium hydroxide (2 ml.) is refluxed for ¾ hour. The reaction solution is cooled to room temperature and diluted with water. The solution is washed three times with ether, chilled in an ice-bath, rendered acidic with concentrated hydrochloric acid, and filtered. The solid material is recrystallized from benzene-hexane (temperature kept below 60° C.). The product obtained is α-methyl-5-phenylpyrazineacetic acid; m.p. 105°–107° C. dec.

EXAMPLE X

Concentrated ammonium hydroxide (80 ml.) added to ethyl α-methylpyrazineacetate (8.0 g., 0.044 mole) at ice-bath temperature. The mixture is stirred at room temperature for 2 hours, and then is saturated with sodium chloride and extracted with chloroform several times. The combined chloroform extracts are dried and evaporated. The solid material is recrystallized from ethyl acetate. The product obtained is α-methylpyrazineacetamide; m.p. 96°–98° C.

EXAMPLE XI

A mixture of ethyl α-methyl-5-phenylpyrazine-acetate (5.0 g., 0.02 mole) and concentrated ammonium hydroxide (100 ml.) is stirred at room temperature for 3 days in a stoppered flask. The reaction mixture is chilled and filtered. The solid material is recrystallized from benzene. The product obtained is α-methyl-5-phenylpyrazineacetamide; m.p. 152°–154°.

EXAMPLE XII

A 12 g. (0.058 mole) sample of 5-(p-chlorophenyl)-pyrazinol is added to phosphorous oxychloride (40 ml.) containing sulfuric acid (3 drops) in a pressure bottle. The mixture is swirled briefly and heated in the open bottle at 120° C. for ¼ hour to allow the evolution of hydrogen chloride. The bottle is closed and heated at about 125° C. for 4 hours. The bottle is cooled and the contents are poured onto a stirred mixture of 370 ml. of ice-water and 200 ml. of chloroform. The mixture is chilled and slowly neutralized with concentrated ammonium hydroxide; a sufficient quantity of 50% sodium hydroxide is added to render the mixture basic. The mixture is filtered through celite, the layers separated, and the aqueous layer is extracted twice more with chloroform. The combined chloroform extracts are dried and evaporated. The solid material is recrystallized from methanol. The product obtained is 2-chloro-5-(p-chlorophenyl)pyrazine; m.p. 145°-146° C.

EXAMPLE XIII

A sodium hydride-mineral oil suspension (54%; 1.8 g., 0.04 mole) is stirred with three 25 ml. portions of dry hexane, each portion being pipetted out to remove the mineral oil. Dimethylformamide (30 ml., previously distilled and dried over a molecular sieve) is added through a pressure equalized addition funnel while a slow stream of nitrogen is passed through the mixture. The reaction vessel is cooled in an ice-bath and diethyl methylmalonate (7 g., 0.04 mole) is added dropwise to the stirred mixture. After the addition is complete, the ice-bath is replaced by an oil bath and the temperature is raised to 50° C. A solution of 2-chloro-5-(p-chlorophenyl)pyrazine (8 g., 0.0355 mole) in warm dimethylformamide (70 ml.) is added dropwise. After this addition is complete, the mixture is heated for 3 hours during which time the temperature is raised to 120° C.

The reaction mixture is cooled to 80° C. and water (3 ml.) is added. The mixture is concentrated to a small volume. The residual liquid is diluted with 40 ml. of ice-water and extracted with ether several times. The combined ether extracts are washed with 5% hydrochloric acid, then with water, dried, and evaporated. The solid material is recrystallized from hexane. The product obtained is diethyl 5-(p-chlorophenyl)-α-methylpyrazinylmalonate; m.p. 62°-64° C.

EXAMPLE XIV

A mixture of diethyl 5-(p-chlorophenyl)-α-methylpyrazinylmalonate (7.0 g., 0.019 mole) and sodium cyanide (2.0 g., 0.04 mole) in dimethyl sulfoxide (60 ml.) is stirred and heated at 120° C. for ½ hour. The reaction mixture is poured into 200 ml. of ice-water saturated with sodium chloride. The material is extracted several times with ether. The combined ether extracts are washed with water, dried, and evaporated. The crude product is chromatographed on a column of acid washed alumina. Elution with benzene-hexane (1:4 through 4:1), followed by benzene is undertaken. The solid material is recrystallized twice from pentane. The product obtained is ethyl 5-(p-chlorophenyl)-α-methylpyrazineacetate; m.p. 47°-49° C.

EXAMPLE XV

A mixture of ethyl 5-(p-chlorophenyl)-α-methylpyrazineacetate (2.33 g., 0.0080 mole), water (24 ml.), and 50% aqueous sodium hydroxide (6 ml.) is refluxed for 1¼ hours. The reaction mixture is diluted with about 30 ml. of water, washed three times with ether, chilled in an ice-bath, and then acidified with concentrated hydrochloric acid. The solid material is filtered and recrystallized from benzene-hexane (temperature kept below 50° C.). The product obtained is 5-(p-chlorophenyl)-α-methylpyrazineacetic acid; m.p. 111°-112° C. dec.

EXAMPLE XVI

A mixture of ethyl 5-(p-chlorophenyl)-α-methylpyrazineacetate (0.90 g., 0.0031 mole) and concentrated ammonium hydroxide (50 ml.) is stirred in a stoppered flask for 3 days at room temperature. The reaction mixture is chilled and filtered. The solid material is recrystallized from benzene. The product obtained is 5-(p-chlorophenyl)-α-methylpyrazineacetamide; m.p. 192°-193° C.

EXAMPLE XVII

A solution of ethyl α-methyl-5-phenylpyrazineacetate, (3.0 g., 0.012 mole) in ether (30 ml.) is added to a stirred solution of sodium amide (0.5, 0.013 mole) in liquid ammonia (50 ml.) at dry ice-acetone temperature. The mixture is allowed to reflux for ¼ hour. Methyl iodide (1.7 g., 0.012 mole) is added. The mixture is stirred for 1 hour. The ammonia is allowed to evaporate. The residue is diluted with ether. Ammonium chloride is added until the mixture is neutral The mixture is poured into dilute hydrochloric acid. The ether layer is separated and washed successively with sodium bisulfite solution, sodium bicarbonate solution, and water. The ether solution is dried and evaporated. The solid material is recrystallized from pentane. The product obtained is ethyl α,α-dimethyl-5-phenylpyrazineacetate.

EXAMPLE XVIII

Using the procedure of Example XI and replacing ethyl α-methyl-5-phenylpyrazineacetate with an equivalent amount of ethyl α,α-dimethyl-5-phenylpyrazineacetate, the product obtained is α,α-dimethyl-5-phenylpyrazineacetamide.

EXAMPLE XIX

Using the procedure of Example IX and replacing ethyl α-methyl-5-phenylpyrazineacetate with an equivalent amount of ethyl α,α-dimethyl-5-phenylpyrazineacetate, the product obtained is α,α-dimethyl-5-phenyl-pyrazineacetic acid.

EXAMPLE XX

A mixture of ethyl α-methyl-5-phenylpyrazineacetate (3.0 g., 0.012 mole), benzylamine (10 ml.) and powdered ammonium chloride (0.3 g.) is heated on the steam bath for 1 hour. The reaction mixture is washed with water, the water decanted, and the solid residue recrystallized from benzene or from ethanol. The product obtained is α-methyl-5-phenylpyrazine-N-benzylacetamide.

EXAMPLE XXI

A mixture of α-methyl-5-phenylpyrazineacetic acid (3.0 g., 0.013 mole) and thionyl chloride (30 ml.) is stirred and warmed at about 60° for ½ hour. The reaction solution is cooled in an ice-bath. A solution of morpholine (1.2 g., 0.014 mole) in benzene (75 ml., is added. The mixture is warmed on the steam bath for ¼ hour, cooled, and diluted with water. The aqueous mixture is extracted several times with ether. The combined ether extracts are washed with dilute hydrochloric acid, dilute sodium bicarbonate, and water, and then dried and evaporated. The solid residue is recrystallized from benzene. The product obtained is 4-(α-methyl-5-phenylpyrazineacetyl)morpholine.

EXAMPLE XXII

3-Hydroxy-5-phenylpyrazine-2-carboxamide is prepared by the method of Dick, Wood and Logan, J. Chem. Soc., 2131 (1956). The carboxamide is converted to 6-phenylpyrazinol by the method of Jezo and Luzak, Chem. Zvest., 22, 190 (1968), using 80 percent sulfuric acid at 180° C. Using the procedure of Example III and replacing 5-phenylpyrazinol with an equivalent amount of 6-phenylpyrazinol, the product obtained is 2-chloro-6-phenylpyrazine. Using the procedure of Example V and replacing 2-chloro-5-phenylpyrazine with an equivalent amount of 2-chloro-6-phenylpyrazine, the product obtained is diethyl α-methyl-6-phenylpyrazinylmalonate. Using the procedure of Example VI and replacing diethyl α-methyl-5-phenylpyrazinylmalonate with an equivalent amount of diethyl α-methyl-6-phenylpyrazinylmalonate, the product obtained is ethyl α-methyl-6-phenylpyrazineacetate. Using the procedure of Example IX and replacing ethyl α-methyl-5-phenylpyrazineacetate with an equivalent amount of ethyl α-methyl-6-phenylpyrazineacetate, the product obtained is α-methyl-6-phenylpyrazineacetic acid. Using the procedure of Example XI and replacing ethyl α-methyl-5-phenylpyrazineacetate with an equivalent amount of ethyl α-methyl-6-phenylpyrazineacetate, the product obtained is α-methyl-6-phenylpyrazineacetamide.

EXAMPLE XXIII p-Chlorophenylglyoxal hydrate is treated with an aqueous sodium bisulfite solution. The mixture is then heated with an equimolar portion of aminomalonamide dissolved in water. The product obtained is 3-hydroxy-5-(p-chlorophenyl)pyrazine-2-carboxamide. The carboxamide is heated at 180° C. in 80 percent sulfuric acid. The product obtained is 6-(p-chlorophenyl)pyrazinol. Using the procedure of Example III and replacing 5-phenylpyrazinol with an equivalent amount of 6-(p-chlorophenyl)pyrazinol, the product obtained is 2-chloro-6-(p-chlorophenyl)pyrazine. Using the procedure of Example V and replacing 2-chloro-5-phenylpyrazine with an equivalent amount of 2-chloro-6-(p-chlorophenyl)pyrazine, the product obtained is diethyl α-methyl-6-(p-chlorophenyl)pyrazinylmalonate. Using the procedure of Example VI and replacing diethyl α-methyl-5-phenylpyrazinylmalonate with an equivalent amount of diethyl α-methyl-6-(p-chlorophenyl)-pyrazinylmalonate, the product obtained is ethyl α-methyl-6-(p-chlorophenyl)pyrazineacetate. Using the procedure of Example IX and replacing ethyl α-methyl-5-phenylpyrazineacetate with an equivalent amount of ethyl α-methyl-6-(p-chlorophenyl)-pyrazineacetate, the product obtained is α-methyl-6-(p-chlorophenyl)-pyrazineacetic acid. Using the procedure of Example XI and replacing ethyl α-methyl-5-phenylpyrazineacetate with an equivalent amount of ethyl α-methyl-6-(p-chlorophenyl)pyrazineacetate, the product obtained is α-methyl-6-(p-chlorophenyl)pyrazineacetamide.

EXAMPLE XXIV

Using the procedure of Example V and replacing 2-chloro-5-phenylpyrazine with an equivalent amount of 2-chloro-3-phenylpyrazine (prepared by the method of Karmas and Spoerri, J. Am. Chem. Soc., 78, 4071, 1956), the product obtained is diethyl α-methyl-3-phenylpyrazinylmalonate. Using the procedure of Example VI and replacing diethyl α-methyl-5-phenylpyrazinylmalonate with an equivalent amount of diethyl α-methyl-3-phenylpyrazinylmalonate, the product obtained is ethyl α-methyl-3-phenylpyrazine-acetate. Using the procedure of Example IX and replacing ethyl α-methyl-5-phenylpyrazineacetate with an equivalent amount of ethyl α-methyl-3-phenylpyrazineacetate, the product obtained is α-methyl-3-phenylpyrazineacetic acid. Using the procedure of Example XI and replacing ethyl α-methyl-5-phenylpyrazineacetate with an equivalent amount of ethyl α-methyl-3-phenylpyrazineacetate, the product obtained is α-methyl-3-phenylpyrazineacetamide.

EXAMPLE XXV

2-Chloro-3-(p-chlorophenyl)pyrazine is prepared by the method of Karmas and Spoerri. (loc. cit.), using 3-(p-chlorophenyl)pyrazinol as the starting material. Starting with this material and using the procedures of Examples V, VI, IX, and XI, the products obtained are diethyl α-methyl-3-(p-chlorophenyl)pyrazinylmalonate, ethyl α-methyl-3-(p-chlorophenyl)pyrazineacetate, α-methyl-3-(p-chlorophenyl)pyrazineacetic acid, and α-methyl-3-(p-chlorophenyl)pyrazineacetamide.

EXAMPLE XXVI

α-Bromocyclohexane acetyl bromide is prepared by the Hell-Volhard-Zelinsky reaction (Hell, Ber., 14, 891, 1881; Zelinsky, Ber., 20, 2026, 1887; Volhard, Ann., 242, 141, 1887) starting with cyclohexylacetic acid. The α-bromocyclohexane acetyl bromide is reacted with ammonia to produce α-aminocyclohexylacetamide. Equimolecular portions of 30 percent aqueous glyoxal and α-aminocyclohexylacetamide are dissolved in aqueous methanol, and the mixture is treated with sodium hydroxide in the cold. The product obtained is 3-cyclohexylpyrazinol. Starting with this product and using the procedures of Examples III, V, VI, IX, and XI, the products obtained are 2-chloro-3-cyclohexylpyrazine, diethyl α-methyl-3-cyclohexylpyrazinylmalonate, ethyl α-methyl-3-cyclohexylpyrazineacetate, α-methyl-3-cyclohexylpyrazineacetic acid, and α-methyl-3-cyclohexylpyrazineacetamide.

EXAMPLE XXVII

Using the procedure of Example XXIII and replacing p-chlorophenylglyoxal hydrate with an equivalent amount of cyclohexylglyoxal hemihydrate, the product obtained is 3-hydroxy-5-cyclohexylpyrazine-2-carboxamide. The carboxamide is heated at 180° C. in 80 percent sulfuric acid. The product obtained is 6-cyclohexylpyrazinol. Starting with this material and using the procedures of Examples III, V, VI, IX, and XI, the products obtained are 2-chloro-6-cyclohexylpyrazine, diethyl α-methyl-6-cyclohexylpyrazinylmalonate, ethyl α-methyl-6-cyclohexylpyrazineacetate, α-methyl-6-cyclohexylpyrazineacetic acid, and α-methyl-6-cyclohexylpyrazineacetamide.

EXAMPLE XXVIII

Using the procedure of Example I and replacing phenylglyoxal hydrate with an equivalent amount of cyclohexylglyoxal hemihydrate, the product obtained is 5-cyclohexylpyrazinol. Starting with this material and using the procedures of Examples III, V, VI, IX and XI, the products obtained are 2-chloro-5-cyclohexylpyrazine, diethyl α-methyl-5-cyclohexylpyrazinylmalonate, ethyl α-methyl-5-cyclohexylpyrazineacetate, α-methyl- 5-cyclohexylpyrazineacetic acid, and α-methyl-5-cyclohexylpyrazineacetamide.

EXAMPLE XXIX

Using the procedure of Kornblum and Frazier, J. Am. Chem. Soc., 88, 865 (1966), substituted phenylglyoxals, such as p-methylphenylglyoxal, p-methoxyphenylglyoxal, m-chlorophenylglyoxal, o-chlorophenylglyoxal, p-fluorophenylglyoxal, 2,5-dichlorophenylglyoxal, p-trifluoromethylphenylglyoxal, 2,3-dimethylphenylglyoxal, and 2,3-dimethoxyphenylglyoxal, are prepared from the corresponding substituted acetophenones. The substituted phenylglyoxals are used in the preparation of the corresponding 5-(substituted-phenyl)pyrazinols by the procedure of Example II. The 2-chloro-5-(substituted-phenyl)pyrazines are prepared by the method of Example XII. The diethyl α-methyl-5-(substituted-phenyl)pyrazinylmalonates are prepared by the method of Example XIII. The ethyl α-methyl-5-(substituted-phenyl)pyrazineacetates are prepared by the method of Example XIV. The α-methyl-5-(substituted-phenyl)pyrazineacetic acids are prepared by the method of Example XV. The α-methyl-5-(substituted-phenyl)pyrazineacetamides are prepared by the method of Example XVI.

EXAMPLE XXX

Using the procedure of Example XXIII and replacing p-chlorophenylglyoxal with substituted phenylglyoxale such as those identified in Example XXIX, the corresponding 6-(substituted-phenyl)pyrazinols are obtained, correspondingly by the procedures of Examples XII, XIII, XIV, XV, and XVI, the corresponding 2-chloro-6-(substituted-phenyl)pyrazines, diethyl α-methyl-6-(substituted-phenyl)-pyrazinylmalonates, ethyl-α-methyl-6-(substituted-phenyl)-pyrazineacetates, α-methyl-6-(substituted-phenyl)pyrazineacetic acids, and α-methyl-6-(substituted-phenyl)pyrazineacetamides are obtained.

EXAMPLE XXXI

Using the procedure of Karmas and Spoerri (J. Am. Chem. Soc., 78, 4071, 1956), and starting with pyrazinol and substituted phenyldiazonium chlorides, such as p-methylphenyldiazonium chloride, p-methoxyphenyldiazonium chloride, m-chlorophenyldiazonium chloride, o-chlorophenyldiazonium chloride, p-fluorophenyldiazonium chloride, 2,5-dichlorophenyldiazonium chloride, p-trifluoromethylphenyldiazonium chloride, 2,3-dimethylphenyldiazonium chloride, and 2,3-dimethoxyphenyldiazonium chloride, the corresponding 3-(substituted-phenyl)pyrazinols are prepared. Starting with these materials and using the procedures of Examples XII, XIII, XIV, XV, and XVI, the products obtained are the corresponding 2-chloro-3-(substituted-phenyl)pyrazines, diethyl α-methyl-3-(substituted-phenyl)pyrazinylmalonates, ethyl α-methyl-3-(substituted-phenyl)pyrazineacetates, α-methyl-3-(substituted-phenyl)pyrazineacetic acids, and α-methyl-3-(substituted-phenyl)pyrazineacetamides.

EXAMPLE XXXII

Using the procedure of Example XXI and replacing morpholine with an equivalent amount respectively of methylamine, dimethylamine, ethylamine, diethylamine, isopropylamine, and n-butylamine, the corresponding N-methyl-, N,N-dimethyl-, N-ethyl-, N,N-diethyl-, N-isopropyl- and N-n-butyl-acetamides are obtained. Repeating this procedure and replacing α-methyl-5-phenylpyrazineacetic acid with equivalent amounts of α-methyl-6-phenylpyrazineacetic acid and α-methyl-3-phenylpyrazineacetic acid, the corresponding N-substituted amides of these compounds are obtained.

EXAMPLE XXXIII

Using the procedure of Example IV, replacing diethyl methylmalonate with an equivalent amount of diethyl malonate and replacing chloropyrazine with equivalent amounts of 2-chloro-5-phenylpyrazine, 2-chloro-6-phenylpyrazine, 2-chloro-3-phenylpyrazine, 2-chloro-5-cyclohexylpyrazine, 2-chloro-6-cyclohexylpyrazine, 2-chloro-3-cyclohexylpyrazine, 2-chloro-5-(p-chlorophenyl)pyrazine, 2-chloro-6-(p-chlorophenyl)-pyrazine, 2-chloro-3-(p-chlorophenyl)pyrazine, 2-chloro-5-(o-chlorophenyl)pyrazine, 2-chloro-5-(p-fluorophenyl)pyrazine, 2-chloro-5-(p-methoxyphenyl)-pyrazine, 2-chloro-5-(2,5-dichlorophenyl)pyrazine, 2-chloro-5-(p-trifluoromethylphenyl)pyrazine, 2-chloro-5-(p-methylphenyl)pyrazine, 2-chloro-5-(m-chlorophenyl)-pyrazine, and 2-chloro-5-(2,3-dimethoxyphenyl)pyrazine, the corresponding diethyl pyrazinylmalonates are produced. Starting with these compounds and using the procedures of Examples VI, IX and XI, the products obtained are the corresponding ethyl pyrazine-acetates, pyrazineacetic acids, and pyrazineacetamides.

EXAMPLE XXXIV

Using the procedure of Example IV, replacing diethyl methylmalonate with an equivalent amount of diethyl malonate, the product obtained is diethyl pyrazinylmalonate. Starting with this material and using the procedures of Examples VI and IX the products obtained are ethyl pyrazineacetate and pyrazineacetic acid.

EXAMPLE XXXV

Using the procedure of Example XVII and replacing methyl iodide with equivalent amounts of ethyl iodide, isopropyl iodide, and n-butyl iodide, the products obtained are ethyl α-methyl-α-ethyl-5-phenylpyrazineacetate, ethyl α-methyl-α-isopropyl-5-phenylpyrazineacetate, and ethyl α-methyl-α-(n-butyl)-5-phenylpyrazineacetate.

EXAMPLE XXXVI

Using the procedure of Example IX and replacing ethyl α-methyl-5-phenylpyrazineacetate with equivalent amounts of the products of Example XXXV, the products obtained are α-methyl-α-ethyl-5-phenylpyrazineacetic acid, α-methyl-α-isopropyl-5-phenylpyrazineacetic acid and α-methyl-α-(n-butyl)-5-phenylpyrazineacetic acid.

EXAMPLE XXXVII

Using the procedure of Example XI and replacing ethyl α-methyl-5-phenylpyrazineacetate with equivalent amounts of the products of Example XXXV, the products obtained are α-methyl-α-ethyl-5-phenylpyrazineacetamide, α-methyl-α-isopropyl-5-phenylpyrazineacetamide, and α-methyl-α-(n-butyl)-5-phenylpyrazineacetamide.

EXAMPLE XXXVIII

Using the procedure of Example V, employing 2-chloro-R-pyrazines having the formula

wherein R has the same value as in Formula I hereinabove, and replacing diethyl methylmalonate with equivalent amounts of diethyl ethylmalonate, diethyl isopropylmalonate, and diethyl n-butylmalonate, the products obtained are diethyl α-substituted-R-pyrazinylmalonates having the formula

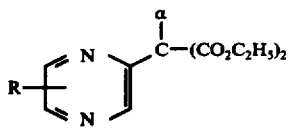

wherein R has the same value as above and α is respectively ethyl, isopropyl, and n-butyl. Starting with these products and using the procedure of Example VI, the products obtained are the corresponding ethyl α-substituted-R-pyrazineacetates. Starting with these products and using the procedures of Examples IX and XI, the corresponding acetic acids and acetamides are obtained.

EXAMPLE XXXIX

Using the procedure of Example XVII, employing the ethyl α-substituted-R-pyrazineacetates of Example XXXVIII, and replacing methyl iodide with equivalent amounts of ethyl iodide, isopropyl iodide, and n-butyl iodide, the products obtained are the ethyl $\alpha^1$, $\alpha^2$-di-substituted-R-pyrazineacetates having the structural formula

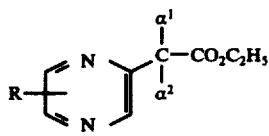

wherein R has the same value as in Formula I hereinabove and wherein $\alpha^1$ and $\alpha^2$ are the following:

| $\alpha^1$ | $\alpha^2$ |
|---|---|
| ethyl | ethyl |
| isopropyl | ethyl |
| n-butyl | ethyl |
| isopropyl | isopropyl |
| isopropyl | n-butyl |
| n-butyl | n-butyl |

The corresponding $\alpha^1$, $\alpha^2$-disubstituted-R-pyrazineacetic acids are prepared by the method of Example IX. The corresponding $\alpha^1,\alpha^2$-disubstituted-R-pyrazineacetamides are prepared by the method of Example XI.

EXAMPLE XL

Sodium hydride (54% in mineral oil; 6.1 g., 0.14 mole) is stirred with three portions (60 ml.) of dry hexane, each portion being pipetted out to remove the mineral oil. Dimethylformamide (previously distilled and dried over a molecular sieve; 55 ml.) is added through a pressure-equalized addition funnel while a slow stream of nitrogen is passed through the mixture. The reaction vessel is placed in an ice-bath and diethyl methylmalonate (24 g., 0.14 mole) is added dropwise to the stirred mixture. After the addition is complete, the ice-bath is replaced by an oil bath and the temperature is raised to 50° C. A solution of 5-chloro-2,3-diphenylpyrazine (28 g., 0.11 mole) in warm dimethylformamide (110 ml.) is added dropwise. The mixture is heated for 3½ hours while the temperature is raised to 120° C.

The reaction mixture is cooled to about 80° C. and water (8 ml.) is added. The mixture is concentrated to a small volume, and the residual liquid is mixed with 800 g. of ice and extracted several times with ether. The combined ether extracts are washed with 5% hydrochloric acid, then with water, dried, and evaporated. The resulting oil is chromatographed on a column of acid-washed alumina. Elution with benzene-hexane (3:2 through 100% benzene) is undertaken. The product obtained is diethyl α-methyl-5,6-diphenylpyrazinylmalonate.

EXAMPLE XLI

A mixture of diethyl α-methyl-5,6-diphenylpyrazinylmalonate, (4.5 g., 0.011 mole) and sodium cyanide (1.1 g., 0.023 mole) in dimethyl sulfoxide (40 ml.) is stirred and heated between 140°–165° C. for 1 hour. The reaction mixture is poured onto 100 g. of ice, saturated with sodium chloride, and extracted several times with ether. The combined ether extracts are washed with water, dried, and evaporated. The resulting oil is purified by elution on a column of acid washed alumina with benzene-hexane (4:1 thru 100% benzene). The product obtained is ethyl α-methyl-5,6-diphenylpyrazineacetate.

EXAMPLE XLII

Concentrated ammonium hydroxide (250 ml.) is added to a solution of ethyl α-methyl-5,6-diphenylpyrazineacetate (9.0 g., 0.027 mole) in absolute ethanol (250 ml.), and the mixture is stirred in a stoppered flask for 5 days. The mixture is kept at room temperature with occasional warming to 50° C. Additional concentrated ammonium hydroxide (100 ml.) is added to the stirring mixture on the fourth day. The stopper is removed, the mixture is diluted with another 100 ml. of concentrated ammonium hydroxide, and then warmed at 50° C. for 15 minutes. The mixture is chilled and filtered. The ammoniacal ethanol filtrate is diluted with a large volume of water. Sodium chloride is added, and the mixture is extracted several times with chloroform. The chloroform solution is dried and evaporated. The solid material is chromatographed on a column of 225 g. of acid washed alumina. Subsequent fractions are eluted with ethyl acetate and with ethyl acetate-methanol (9/1). The purest fraction is recrystallized from ethanol-water. The product obtained is α-methyl-5,6-diphenylpyrazineacetamide; m.p. 123°–125° C.

EXAMPLE XLIII

A mixture of ethyl α-methyl-5,6-diphenylpyrazineacetate (1.4 g., 0.004 mole), 95% ethanol (20 ml.), water (3 ml.), and 50% sodium hydroxide (3 ml.) is refluxed for 4 hours. The ethanol is evaporated and the aqueous residue is diluted with water and washed several times with ether. The aqueous layer is acidified in the cold with concentrated hydrochloric acid. The product is filtered and purified by careful recrystallization from ether-hexane or by dissolving in aqueous base and reforming with concentrated acid. The product obtained is α-methyl-5,6-diphenylpyrazineacetic acid; m.p. 127°-128° C. dec.

EXAMPLE XLIV

A mixture of diethyl α-methyl-5-phenylpyrazinylmalonate (4 g., 0.012 mole) in water (32 ml.) containing 50% sodium hydroxide (8 ml.) is stirred and refluxed for 1¼ hours. The solution is evaporated to about half the original volume and chilled. The crystals formed are the disodium salt of α-methyl-5-phenylpyrazinylmalonic acid. Repeating the process but acidifying the solution after refluxing, and then adding sodium hydroxide, evaporating to half the original volume and chilling, the sodium salt of α-methyl-phenylpyrazineacetic acid is recovered. These procedures are repeated using ammonium hydroxide and calcium hydroxide respectively and adjusting the reflux time to obtain the corresponding ammonium and calcium salts of α-methyl-5-phenylpyrazinylmalonic acid and α-methyl-5-phenylpyrazineacetic acid. In a similar manner, the salts of the other malonic acids and acetic acids of this invention are prepared.

EXAMPLE XLV

A quantity of α-methyl-5,6-diphenylpyrazineacetic acid is heated at about 130° C. for fifteen minutes. The resulting melt is diluted with water and extracted several times with ether. The ether solution is dried and evaporated. The solid material is recrystallized from 95 percent ethanol. The product obtained is 2,3-diphenyl-5-ethylpyrazine; m.p. 102°-104° C.

EXAMPLE XLVI

Using the procedures of Example XXVI and thereafter Examples III, V, VI, IX, and XI as shown in Example XXVI, and replacing cyclohexylacetic acid with an equivalent amount of cyclopentylacetic acid, the products obtained are 3-cyclopentylpyrazinol, 2-chloro-3-cyclopentylpyrazine, diethyl α-methyl-3-cyclopentylpyrazinylmalonate, ethyl α-methyl-3-cyclopentylpyrazineacetate, α-methyl-3-cyclopentylpyrazineacetic acid, and α-methyl-3-cyclopentylpyrazineacetamide.

EXAMPLE XLVII

Using the procedure of Example XXVII and thereafter Examples III, V, VI, IX and XI as shown in Example XXVII, and replacing cyclohexylglyoxal with an equivalent amount of cyclopentylglyoxal, the products obtained are 6-cyclopentylpyrazinol, 2-chloro-6-cyclopentylpyrazine, diethyl α-methyl-6-cyclopentylpyrazinylmalonate, ethyl α-methyl-6-cyclopentylpyrazineacetate, α-methyl-6-cyclopentylpyrazineacetic acid, and α-methyl-6-cyclopentylpyrazineacetamide.

EXAMPLE XLVIII

Using the procedure of Example XXVIII and thereafter Examples III, V, VI, IX, and XI as shown in Example XXVIII, and replacing cyclohexylglyoxal with an equivalent amount of cyclopentylglyoxal, the products obtained are 5-cyclopentylpyrazinol, 2-chloro-5-cyclopentylpyrazine, diethyl α-methyl-5-cyclopentylpyrazinylmalonate, ethyl α-methyl-5-cyclopentylpyrazineacetate, α-methyl-5-cyclopentylpyrazineacetic acid, and α-methyl-5-cyclopentylpyrazineacetamide.

EXAMPLE XLIX

A mixture of diethyl α-ethyl-5-phenylpyrazinylmalonate (18 g., 0.053 mole), 40 ml. of 50 percent sodium hydroxide, and 160 ml. of water is refluxed for 2 hours. The mixture is then diluted with water, washed several times with ether, and acidified with cold concentrated hydrochloric acid. The solid material is recovered by filtration and crystallized from benzene-hexane below 50° C. The product is α-ethyl-5-phenylpyrazineacetic acid; m.p. 90°-91° C. dec.

EXAMPLE L

Using the procedure of Example XL, replacing diethyl methylmalonate with an equivalent amount of diethyl ethylmalonate, the product obtained is diethyl α-ethyl-5,6-diphenylpyrazinylmalonate. Starting with this product and using the procedures of Examples XLI, XLIII, and XLII, the corresponding acetate, acetic acid, and acetamide are obtained.

Table I is the ultraviolet light absorption characteristics of the compounds identified in the Examples. The solvent employed is methanol.

TABLE I

| Example No. | $\lambda_{max.}$ ($\mu$) | $\epsilon$ |
|---|---|---|
| IV | 263 | 7,700 |
|  | 269* | 6,500 |
|  | 306 | 1,100 |
| V | 251 | 15,400 |
|  | 288 | 14,500 |
| VI | 249 | 14,400 |
|  | 290 | 11,600 |
| VII | 265 | 7,000 |
|  | 270* | 5,800 |
|  | 308 | 790 |
| VIII | 267 | 6,700 |
|  | 272* | 6,100 |
|  | 307 | 910 |
| IX | 249 | 15,600 |
|  | 289 | 12,200 |
| X | 266 | 7,000 |
|  | 271* | 6,300 |
|  | 309 | 970 |
| XI | 249 | 15,400 |
|  | 290 | 12,300 |
| XIII | 255 | 18,600 |
|  | 287 | 19,200 |
|  | 305* | 13,900 |
| XIV | 254 | 16,900 |
|  | 288 | 15,600 |
|  | 305* | 11,800 |
| XV | 254 | 18,000 |
|  | 288 | 16,100 |
|  | 300* | 13,000 |
| XVI | 254 | 17,600 |
|  | 288 | 16,300 |
|  | 300* | 13,200 |
| XL | 222 | 26,500 |
|  | 270* | 11,700 |
|  | 283 | 12,100 |
|  | 310* | 10,100 |
| XLI | 220 | 22,800 |
|  | 267 | 11,000 |
|  | 293 | 11,000 |
|  | 308* | 10,000 |
| XLII | 220 | 23,400 |
|  | 265 | 11,500 |
|  | 292 | 11,300 |
|  | 310* | 9,850 |
| XLV | 219 | 20,200 |
|  | 263 | 10,400 |
|  | 295 | 10,100 |
|  | 310* | 8,850 |
| XLIII | 219 | 21,400 |
|  | 266 | 10,400 |
|  | 294 | 10,700 |
|  | 310* | 9,300 |
| XLIX | 250 | 14,900 |
|  | 290 | 12,000 |

*shoulder

Certain of the novel compounds of this invention have been found to possess pharmacological activity as antiinflammatory agents. These are identified by Example number in Table II. The test used is known as the kaolin-induced gas edema test. This test measures the ability of a compound, when administered in a single oral dose, to inhibit the swelling of the rat paw injected with a standard amount (0.1 ml.) of 10% kaolin suspension in saline. For comparative purposes, the activity of the compound to be tested is measured against that produced by the known anti-inflammatory agent, phenylbutazone. In this assay, the test compound (0.4% suspension or 0.4% solution, depending on the compound) and phenylbutazone (0.4% solution) are administered in saline. Male Holtzman rats are used in the assay. The results are recorded in terms of percent inhibition produced by the compound and by phenylbutazone. The percent inhibition is calculated from the milliliters of mercury displaced as the edema develops in the paw. The paw is placed in a pool of mercury immediately after injection with the kaolin suspension, and a reading is taken on the quantity of mercury displaced. The animal is then returned to the cage, allowing the edema to develop. After six hours, the paw is again immersed in mercury and the quantity of mercury displaced is again measured. The method is described in J. Pharm. and Experimental Therapeutics, 162, 196–201 (1968).

Table II

| Example | No. of Rats | Dose (oral) Mg/Kg | | Inhibition | |
| --- | --- | --- | --- | --- | --- |
| | | Example | Phenyl-butazone | Example | Phenyl-butazone |
| IV | 10 | 100 | 100 | 16 | 43 |
| V | 10 | 100 | 100 | 50 | 47 |
| VI | 10 | 100 | 100 | 40 | 53 |
| IX | 10 | 100 | 100 | 50 | 34 |
| XI | 10 | 100 | 100 | 38 | 34 |
| XIII | 10 | 100 | 100 | 41 | 50 |
| XIV | 10 | 100 | 100 | 27 | 44 |
| XV | 10 | 100 | 100 | 41 | 61 |
| XVI | 10 | 100 | 100 | 56 | 48 |
| XLIX | 10 | 100 | 100 | 21 | 41 |

We claim:
1. 2,3-diphenyl-5-ethylpyrazine.

* * * * *